(12) United States Patent
Petito et al.

(10) Patent No.: US 6,476,005 B1
(45) Date of Patent: Nov. 5, 2002

(54) ORAL AND INJECTABLE NUTRITIONAL COMPOSITION

(76) Inventors: George D. Petito, 1890 Bucknell Dr., Bethlehem, PA (US) 18015; Anita M. Petito, 1890 Bucknell Dr., Bethlehem, PA (US) 18015

( * ) Notice: Subject to any disclaimer, the term of this patent is extended or adjusted under 35 U.S.C. 154(b) by 0 days.

(21) Appl. No.: 09/360,169

(22) Filed: Jul. 26, 1999

Related U.S. Application Data

(63) Continuation-in-part of application No. 09/046,710, filed on Mar. 24, 1998, now abandoned.

(51) Int. Cl.[7] ............... A61K 31/7008; A61K 38/16; A61K 35/32
(52) U.S. Cl. .............. 514/62; 514/21; 514/54; 514/55; 514/61; 424/499; 424/548; 424/639; 426/648; 426/656; 426/658
(58) Field of Search ............... 514/21, 55, 54, 514/61, 62; 424/639, 499, 548; 426/648, 650, 656, 658

(56) References Cited

U.S. PATENT DOCUMENTS

| | | | |
|---|---|---|---|
| 1,950,100 A | 3/1934 | Crandall, Jr. | 167/68 |
| 4,006,224 A | 2/1977 | Prudden | 424/180 |
| 4,216,204 A | 8/1980 | Robertson | 424/95 |
| 4,455,302 A | 6/1984 | Robertson | 424/177 |
| 5,141,928 A | 8/1992 | Goldman | 514/54 |
| 5,252,339 A | 10/1993 | Christofori et al. | 424/479 |
| 5,364,845 A | 11/1994 | Henderson | 514/54 |
| 5,442,053 A | 8/1995 | della Valle et al. | 536/55.1 |
| 5,498,606 A | 3/1996 | Soll et al. | 514/54 |
| 5,587,363 A | 12/1996 | Henderson | 514/54 |
| 5,840,715 A | 11/1998 | Florio | 514/62 |
| 5,929,050 A * | 7/1999 | Petito | 514/54 |

FOREIGN PATENT DOCUMENTS

| | | |
|---|---|---|
| DE | 3445324 | 12/1986 |
| FR | 2035781 | 12/1970 |
| GB | 869940 | 5/1962 |

OTHER PUBLICATIONS

Sigma Catalog, p. 459, 1993.*
PROMT abstract of Body Ammo Supplement—Joint Connection Capsules, Product Alert, Oct. 1997.*
PROMT abstract of Arthred–G hydrolyzed collagen protein with glucosamine & chondroitin sulfate powdered dietary supplement—Product Alert, Jul. 1997.*
Merck Index—10th edition, entry #2297, 1983.*
Merck Index—12th edition, entry #5747, 1996.*
Ansel, H. et al, ed. "Pharmaceutical Dosage Forms and Drug Delivery" chap. 8, pp. 286–336, 1995.*

* cited by examiner

Primary Examiner—James O. Wilson
Assistant Examiner—Leigh C. Maier
(74) Attorney, Agent, or Firm—Richard C. Litman

(57) ABSTRACT

An oral and injectable composition for mammals comprising a salt of glucosamine, such as glucosamine hydrochloride, sulfate, nitrate, or iodide, a chondroitin sulfate, hydrolyzed or native collagen, a sodium hyaluronate, chelated manganese ascorbate, and L-malic acid in powder form for oral ingestion or in a solution of sterilized water for injection. The composition acts as a chondroprotective agent which provides foundational support for the creation of new body tissue and cartilage growth in humans and animals. Other beneficial physiological properties include the enhancement of chondrocyte synthesis, the healing of chronic or acute wounds, the maintenance of healthy muscle and tissue, increasing the desirable concentration of hyaluronic acid, and anti-inflammatory activity.

9 Claims, No Drawings

ORAL AND INJECTABLE NUTRITIONAL COMPOSITION

REFERENCE TO RELATED PATENT APPLICATION

This application is a continuation-in-part of application Ser. No. 09/046,710 filed Mar. 24, 1998, now abandoned.

BACKGROUND OF THE INVENTION

1. Field of the Invention

The present invention relates to an oral and injectable nutritional composition in powder or aqueous form for mammalian use comprising glucosamine or a glucosamine salt, chondroitin sulfate, hydrolyzed collagen, sodium hyaluronate, a manganese salt, and, optionally, L-malic acid. Phosphate salts are excluded from this nutritional composition.

2. Description of the Related Art

The related art of interest describes various oral and topical products for improving various physiological functions of the human body. The related art will be discussed in the order of perceived relevance to the present invention.

U.S. Pat. No. 5,141,928 issued on Aug. 25, 1992, to Lawrence Goldman describes ophthalmic medications containing glycosaminoglycan polysulfates (GAGPS) or mucopolysaccharides having a molecular weight in the range of 5,000 to 20,000 Daltons combined with antibiotics for treating eye infections and antimicrobial agents such as pilocarpine or epinephrine for glaucoma. GAGPS include chondroitin sulfate and hyaluronic acid that contain hexosamines. The medicament composition is thus distinguishable from the present invention prohibiting sulfates for its reliance on glycosaminoglycan polysulfates, antibiotics, and antimicrobial agents, which composition is limited to human use.

U.S. Pat. No. 1,950,100 issued on Mar. 6, 1934, to Lathan A. Crandall, Jr. describes a chemical composition for the treatment of migraine, urticarial eruptions, peptic ulcers, and multiple sclerosis, inter alia. Chondroitin sulfate is combined either calcium, magnesium or iron. The composition is distinguishable for its sole ingredient containing a sulfate which is useful for only other human ailments.

U.S. Pat. No. 5,364,845 issued on Nov. 15, 1994 and U.S. Pat. No. 5,587,363 issued Dec. 24, 1996, both to Robert W. Henderson describes a therapeutic composition administered in capsules for the protection, treatment and repair of connective tissue in mammals. The composition contains 250–3000 mg glucosamine hydrochloride or sulfate, 50–1000 mg chondroitin sulfate, and can additionally comprise 15–950 mg manganese ascorbate. The composition is distinguishable from the present invention for not requiring hydrolyzed or native collagen, sodium hyaluronate, and L-malic acid.

U.S. Pat. No. 5,840,715 issued on Nov. 24, 1998 to Florio teaches a dietary regimen of nutritional supplements for relief of symptoms of arthritis. The dietary regimen comprises gamma linolenic acid (GLA), a mixture of eicosapentaenoic acid and docosahexaneoic acid (EPA) and a mixture of chondroitin sulfate, glucosamine. sulfate and manganese asparate.

U.S. Pat. No. 5,438,043 issued on Aug. 1, 1995, to Olle Ljungqvist describes a hypotonic solution for ingestion by patients undergoing surgery for suppressing insulin resistance. The solution contains dextrin, maltose, glucose, sodium chloride, and sodium hydroxide at a pH between 5.6 and 6.8. The composition is distinguishable for its absence of every ingredient of the present invention.

U.S. Pat. No. 5,498,606 issued on Mar. 12, 1996, to David B. Soll describes a topical application or injection of 40–55 wt. % chondroitin sulfate in solution prior to or during surgery in internal human and animal tissues, organs and body cavities. The composition protects the joint cells, reduces aseptic inflammation and/or preserves human and animal cells and tissues in vitro for later in vivo use. The therapeutic composition is distinguishable for its reliance only on chondroitin sulfate.

U.S. Pat. No. 4,837,024 issued on Jun. 6, 1989, to Michaeli describes topical compositions for improving wound healing comprising a suspension of particles of collagen and a glycosaminoglycan. The composition is useful for treating surface wounds by applying the composition to a gauze, bandage, fabric, tape or the like.

U.S. Pat. No. 5,442,053 issued on Aug. 15, 1995, to Francesco della Valle et al. describes a pharmaceutical composition and method for treating ophthalmic conditions, dermatological conditions, diseases of the mucous of the oral and nasal cavities or diseases of the outer ear by administering a salt of hyaluronic acid (alkali, alkali metal, magnesium, aluminum or ammonium) combined with a pharmacologically active substance such as erythromycin. The hyaluronic acid fraction has an average molecular weight of 30,000 to 730,000. The topical medicament can be applied as solids or in solution. The pharmaceutical composition is distinguishable for its reliance on only hyaluronic acid salt and a multitude of pharmacological substances for ophthalmic use.

U.S. Pat. No. 4,216,204 issued on Aug. 5, 1980, and U.S. Pat. No. 4,455,302 issued on Jun. 19, 1984, to Harry J. Robertson both describe a medical protein hydrolysate containing an acetic acid extract of polypeptides and amino acids in the form of powder or a gel and produced from poultry feet. An aqueous solution can also be injected into a wound area such as burned animal regions. The composition is useful for regrowing muscle, skin and nerve tissue. The composition is distinguishable for its limitation to only the protein hydrolysate.

U.S. Pat. No. 4,006,224 issued on Feb. 1, 1977, to John F. Prudden describes a method and agent for treating inflammatory disorders of the gastrointestinal tract by administering 20 to 300 mg per Kg of body weight per day of D-glucosamine hydrochloride in either solid or liquid form. Lactose and corn starch can be added for tablets. The composition is distinguishable for its limitation to only D-glucosamine hydrochloride for treating gastrointestinal problems.

U.S. Pat. No. 5,252,339 issued on Oct. 12, 1993, to Manlio Cristofori et al. describes pharmaceutical compositions for oral intake containing glycosaminoglycan sulfate such as heparin, a thickening substance such as gum arabic, and a surfactant such as sodium cholate. The compositions make possible the absorption of the glycosaminoglyan sulfate in the intestine for performance of their anticoagulant, fibrinolytic, antithrombotic, antiathero-sclerotic, and antiperlipoproteinemic properties. The compositions are distinguishable for utilizing only one ingredient of the present invention.

French Patent Application No. 2.035.781 published on Dec. 24, 1970, for Jean Dumazert describes a glucosamine-based medicament containing glucosamine chlorohydrate or acetyl glucosamine and a lipotropic agent such as either betaine, methionine or choline. The medicament is distinguishable for containing only glucosamine chlorohydrate and a lipotropic agent which are not in the present invention.

German Patent Application No. 3445324 published on Jun. 12, 1986, for Erich Enghofer et al. describes a synergistic composition for treatment of arthritis and contains glucosamine and an anti-exudative venous agent such as aescin or hydroxyethyl-rutoside. The composition is distinguishable for showing only glucosamine and requiring an anti-exudative venous agent.

U.K. Patent Application No. 896,940 published on May 23, 1962, for Chas. Pfizer & Co. describes a healing agent for wounds of the body surface containing glucosamine and/or N-acetylglucosamine and glucosamine phosphate in a saline solution. The composition is distinguishable for requiring a phosphate salt of glucosamine.

None of the above inventions and patents, taken either singularly or in combination, is seen to describe the instant invention as claimed. Thus, an oral and injectable nutritional product which contain the necessary ingredients for healing wounds of humans and animals is desirable.

SUMMARY OF THE INVENTION

The present invention is an oral and/or injectable nutritional composition for mammalian use, comprising a glucosamine salt such glucosamine hydrochloride, sulfate, nitrate, or iodide, chondroitin sulfate, hydrolyzed collagen, sodium hyaluronate, and manganese ascorbate. The nutritional composition can be administered in powder, capsule or tablet form for oral ingestion or in a solution of sterilized water for oral ingestion or injection. The composition comprises a chondroprotective agent which provides foundational support for the creation of new body tissue and cartilage growth in humans and animals. Other beneficial physiological properties include the enhancement of chondrocyte synthesis, the maintenance of healthy muscle and tissue, increasing the desirable concentration of hyaluronic acid, and being anti-inflammatory.

Accordingly, it is a principal object of the invention to provide an oral or injectable nutritional composition for promoting the healing of wounds in humans and animals.

It is another object of the invention to provide an oral and injectable nutritional composition for promoting the healing of wounds in humans and animals containing a glucosamine salt such as glucosamine hydrochloride, sulfate, nitrate, or iodide, chondroitin sulfate, hydrolyzed collagen, sodium hyaluronate, and manganese ascorbate.

It is a further object of the invention to provide an injectable nutritional composition for promoting the healing of wounds, i.e., tissue and cartilage repair of either chronic or acute, in humans and animals containing a glucosamine salt such as glucosamine hydrochloride, sulfate, nitrate, or iodide, chondroitin sulfate, hydrolyzed collagen and sodium hyaluronate in a sterile aqueous solution.

Yet another object of the invention is to provide an injectable nutritional composition for promoting the healing of wounds in humans and animals containing a glucosamine salt such as glucosamine hydrochloride, sulfate, nitrate, or iodide, chondroitin sulfate, hydrolyzed collagen, sodium hyaluronate, and L-malic acid.

It is an object of the invention to provide improved elements and arrangements thereof for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENT

The present invention is directed to a composition comprising a chondroprotective agent which provides foundational support for the creation of new body tissue and cartilage growth in mammals such as humans and animals. Other beneficial physiological properties include the enhancement of chondrocyte synthesis, the maintenance of healthy muscle and tissue, increasing the desirable concentration of hyaluronic acid, and anti-inflammatory activity.

It has been found that the following composition has provided the above-mentioned benefits in both animals and humans. The unit dose will be described for a human in terms of dosage per bodyweight. Animals may require larger doses.

(1) A glucosamine salt obtained from either synthetic, bovine or porcine sources having a molecular weight range from 5,000 to 30,000. Suitable salts of the glucosamine include the hydrochloride, sulfate, nitrate and iodide.

(2) Chondroitin sulfate, Type A (chondroitin-4-sulfate), Type B (chrondroitin-5-sulfate), and/or Type C (chondroitin-6-sulfate), obtained through fermentation or extraction of bovine trachea, other bovine or porcine sources. A molecular weight range of 5,000–50,000 can be used, with a preferred range of 25,000–35,000.

(3) Hydrolyzed Type 1 collagen, preferably natural hydrolyzed collagen powder having a pH of 5.5–6.5, an ash content of 2.5% maximum, an isotonic point of 5.0–6.5, and obtained from synthetic, bovine or porcine sources. Preferably, the hydrolyzed Type 1 collagen has a molecular weight average no greater than about 2,000 Daltons, and more preferably, a molecular weight average no greater than about 1,000 to about 1,500 Daltons.

(4) Sodium hyaluronate obtained from either synthetic, bovine or avian sources with a molecular weight range from about 50,000 to about 3,500,000 Daltons.

(5) Chelated manganese ascorbate, U.S.P. food grade.

(6) L-malic acid, U.S.P. food grade, acts as a detoxifying agent by ridding the body of lactic acid often found in connective tissue.

For injectable use, the above substances will be dissolved in sterilized water and buffered with citric acid or sodium chloride to improve shelf life. The pH can be adjusted with conventional agents. Also, preservatives such as ethylenediaminetetraacetic acid (EDTA), benzyl alcohol, and benzalkonium chloride can be added.

Powdered, encapsulated or pilled compositions to be taken orally by either humans or animals are based on mg/kgm bodyweight and described in the following order of (a) a preferred concentration, (b) an optional range and (c) a broad range in terms of the above numbered ingredients (1)–(6).

(1): (a) 5 mg; (b) 3–8 mg; (c) 2–10 mg
(2): (a) 3.5 mg; (b) 1–6 mg; (c) 1–8 mg
(3): (a) 4 mg; (b) 3–15 mg; (c) 2–20 mg
(4): (a) 5 mg; (b) 2–6 mg; (c) 1–7 mg
(5): (a) 1 mg; (b) 0.5 mg; (c) 0.5–3 mg
(6): (a) 5 mg; (b) 0.2 mg; (c) 0.2–6 mg

For injectable use in humans, the following compositions are recommended as a first preference, a second preference and a third preference. First: (1), (2), (4); second: (1)–(4); and third: (1)–(6).

For injectable use in animals, the following compositions are recommended as first, second and third preferences.

First: (1), (2), (4); second: (1), (2), (4), (6); third: (2)–(6); fourth: (1)–(4); and fifth: (1)–(6).

In terms of injectable solutions in weight of ingredient per volume of a sterilized aqueous solution for human and animal, the following preferred concentrations and ranges are: (1) 150 mg/ml, 10–1,000 mg/ml; (2) 150 mg/ml, 5–1,500 mg/ml; (3) 2–100 mg/ml; and (4) 5 mg/ml, 1–30 mg/ml. However, ingredients (5) and (6) can be added.

Unlike the compositions disclosed in the prior art, it is believed that the present composition provides an enhanced chondroprotective effect by providing foundational support for the creation of new body tissue and cartilage growth in mammals because it comprises hydrolyzed Type 1 collagen having a preferred molecular weight average no greater than 2,000 Daltons, more preferably the hydrolyzed Type 1 collagen has a molecular weight average of about 1,000 to 1,500. It is believed that hydrolyzed Type 1 collagen having a preferred molecular weight average no greater than about 2,000 Daltons, acts as a transporter or carrier for the larger molecules of sodium hyaluronate and/or chondroitin sulfate by aiding in the absorption process of these large molecules, thereby increasing the bio-availability of each.

It is to be understood that the present invention is not limited to the embodiment described above, but encompasses any and all embodiments within the scope of the following claims.

We claim:

1. An orally ingestible composition for use in mammals consisting of the following ingredients in mg/kg of bodyweight:
   a glucosamine salt in a range of about 2–10 mg/kg, said glucosamine salt being selected from the group consisting of hydrochloride, sulfate, nitrate, and iodide;
   chondroitin sulfate in a range of about 1–8 mg/kg;
   hydrolyzed collagen in a range of about 2–20 mg/kg;
   sodium hyaluronate in a range of about 1–7 mg/kg;
   a chelated manganese salt in a range of about 0.5–3 mg/kg; and
   L-malic acid in a range of about 0.2–6 mg/kg, said L-malic acid acting as a detoxifying agent.

2. The composition according to claim 1, wherein the hydrolyzed collagen is hydrolyzed Type 1 collagen having an average molecular weight of about no greater than 2,000 Daltons.

3. The composition according to claim 2, wherein the hydrolyzed collagen is hydrolyzed Type 1 collagen having an average molecular weight of about no greater than 1,500 Daltons.

4. The oral nutritional powder composition according to claim 1, wherein the ingredients have the following ranges in mg/kg of bodyweight:
   3–8 mg/kg of glucosamine salt;
   1–6 mg/kg of chondroitin sulfate;
   3–15 mg/kg of hydrolyzed collagen;
   2–6 mg/kg of sodium hyaluronate;
   0.5–1 mg/kg of manganese ascorbate; and
   0.2–1 mg/kg of L-malic acid.

5. The composition according to claim 1, wherein the composition is a dosage form selected from the group consisting of a powder, capsule or tablet.

6. An injectable composition for use in mammals consisting of the following ingredients in an aqueous solution in mg/kg of bodyweight:
   a glucosamine salt in a range of 2–10 mg/kg, said glucosamine salt being selected from the group consisting of hydrochloride, sulfate and nitrate;
   chondroitin sulfate in a range of 1–8 mg/kg;
   hydrolyzed collagen in a range of 2–20 mg/kg;
   sodium hyaluronate in a range of 1–7 mg/kg;
   a chelated manganese salt in a range of 0.5–3 mg/kg;
   L-malic acid in a range of about 0.2–6 mg/kg, said L-malic. acid acting as a detoxifying agent; and
   sterile water.

7. The injectable composition according to claim 6, wherein the hydrolyzed collagen is hydrolyzed Type 1 collagen having an average molecular weight of about no greater than 2,000 Daltons.

8. The injectable composition according to claim 6, wherein the hydrolyzed collagen is hydrolyzed Type 1 collagen having an average molecular weight of about no greater than 1,500 Daltons.

9. The injectable composition according to claim 6, wherein the ingredients have the following ranges in mg/kg of bodyweight:
   3–8 mg/kg of glucosamine salt;
   1–6 mg/kg of chondroitin sulfate;
   3–15 mg/kg of hydrolyzed collagen;
   2–6 mg/kg of sodium hyaluronate;
   0.5–1 mg/kg of manganese ascorbate; and
   0.2–1 mg/kg of L-malic acid.

* * * * *